United States Patent
Margiotta, Jr.

(10) Patent No.: US 6,244,266 B1
(45) Date of Patent: Jun. 12, 2001

(54) COLD WEATHER AIR WARMING APPARATUS

(76) Inventor: Victor G. Margiotta, Jr., P.O. Box 792, Verplanck, NY (US) 10596

( * ) Notice: Subject to any disclaimer, the term of this patent is extended or adjusted under 35 U.S.C. 154(b) by 0 days.

(21) Appl. No.: 09/258,339

(22) Filed: Feb. 25, 1999

(51) Int. Cl.[7] ................................................. A61M 16/00
(52) U.S. Cl. ............................... 128/201.13; 128/200.24; 128/205.27; 128/205.29; 128/201.17
(58) Field of Search .......................... 128/204.17, 201.13, 128/200.24, 205.27, 205.29

(56) References Cited

U.S. PATENT DOCUMENTS

| 3,491,754 | * | 1/1970 | Weese | 128/212 |
| 3,707,966 | * | 1/1973 | Nebel | 128/212 |
| 4,196,728 | * | 4/1980 | Granite | 128/201.13 |
| 4,294,242 | * | 10/1981 | Cowans | 128/201.13 |
| 4,441,494 | * | 4/1984 | Montalbano | 128/204.17 |
| 4,683,869 | * | 8/1987 | Wilcox | 126/204 |

* cited by examiner

Primary Examiner—Glenn K. Dawson
Assistant Examiner—Mital Patel

(57) ABSTRACT

A cold weather air warming apparatus for permitting a user to breathe air warmed by the body. The cold weather air warming apparatus includes a mouthpiece that has a mouth engaging portion, a coupling portion, and a lumen extending through opposite ends of the mouthpiece. A length of body tubing has opposite open first and second ends. The first end of the body tubing is coupled to the coupling portion of the mouthpiece. The length of body tubing is flexible and adapted for wrapping around a torso of a user, the open second end of the length of body tubing is in communication with the lumen of the mouthpiece.

14 Claims, 2 Drawing Sheets

COLD WEATHER AIR WARMING APPARATUS

BACKGROUND OF THE INVENTION

1. Field of the Invention

The present invention relates to air warming devices and more particularly pertains to a new cold weather air warming apparatus for permitting a user to breathe air warmed by the body.

2. Description of the Prior Art

The use of air warming devices is known in the prior art. More specifically, air warming devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,029,572; 2,460,269; 4,461,292; 2,551,142; 3,153,720; and 3,229,681.

While these devices fulfill their respective, particular objectives and requirements, the aforementioned patents do not disclose a new cold weather air warming apparatus. The inventive device includes a mouthpiece that has a mouth engaging portion, a coupling portion, and a lumen extending through opposite ends of the mouthpiece. A length of body tubing has opposite open first and second ends. The first end of the body tubing is coupled to the coupling portion of the mouthpiece. The length of body tubing is flexible and adapted for wrapping around a torso of a user, the open second end of the length of body tubing is in communication with the lumen of the mouthpiece.

In these respects, the cold weather air warming apparatus according to the present invention substantially departs from the conventional concepts and designs of the prior art, and in so doing provides an apparatus primarily developed for the purpose of permitting a user to breathe air warmed by the body.

SUMMARY OF THE INVENTION

In view of the foregoing disadvantages inherent in the known types of air warming devices now present in the prior art, the present invention provides a new cold weather air warming apparatus construction wherein the same can be utilized for permitting a user to breathe air warmed by the body.

The general purpose of the present invention, which will be described subsequently in greater detail, is to provide a new cold weather air warming apparatus apparatus and method which has many of the advantages of the air warming devices mentioned heretofore and many novel features that result in a new cold weather air warming apparatus which is not anticipated, rendered obvious, suggested, or even implied by any of the prior art air warming devices, either alone or in any combination thereof.

To attain this, the present invention generally comprises a mouthpiece that has a mouth engaging portion, a coupling portion, and a lumen extending through opposite ends of the mouthpiece. A length of body tubing has opposite open first and second ends. The first end of the body tubing is coupled to the coupling portion of the mouthpiece. The length of body tubing is flexible and adapted for wrapping around a torso of a user, the open second end of the length of body tubing is in communication with the lumen of the mouthpiece.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the inventions in any way.

It is therefore an object of the present invention to provide a new cold weather air warming apparatus apparatus and method which has many of the advantages of the air warming devices mentioned heretofore and many novel features that result in a new cold weather air warming apparatus which is not anticipated, rendered obvious, suggested, or even implied by any of the prior art air warming devices, either alone or in any combination thereof.

It is another object of the present invention to provide a new cold weather air warming apparatus which may be easily and efficiently manufactured and marketed.

It is a further object of the present invention to provide a new cold weather air warming apparatus which is of a durable and reliable construction.

An even further object of the present invention is to provide a new cold weather air warming apparatus which is susceptible of a low cost of manufacture with regard to both materials and labor, and which accordingly is then susceptible of low prices of sale to the consuming public, thereby making such cold weather air warming apparatus economically available to the buying public.

Still yet another object of the present invention is to provide a new cold weather air warming apparatus which provides in the apparatuses and methods of the prior art some of the advantages thereof, while simultaneously overcoming some of the disadvantages normally associated therewith.

Still another object of the present invention is to provide a new cold weather air warming apparatus for permitting a user to breathe air warmed by the body.

Yet another object of the present invention is to provide a new cold weather air warming apparatus which includes a mouthpiece that has a mouth engaging portion, a coupling portion, and a lumen extending through opposite ends of the mouthpiece. A length of body tubing has opposite open first and second ends. The first end of the body tubing is coupled to the coupling portion of the mouthpiece. The length of body tubing is flexible and adapted for wrapping around a torso of a user, the open second end of the length of body tubing is in communication with the lumen of the mouthpiece.

Still yet another object of the present invention is to provide a new cold weather air warming apparatus that helps prevent chilling of the lungs when exercising in cold weather.

Even still another object of the present invention is to provide a new cold weather air warming apparatus that includes a valve system to prevent stale air from being recycled through the tube and re-inhaled.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
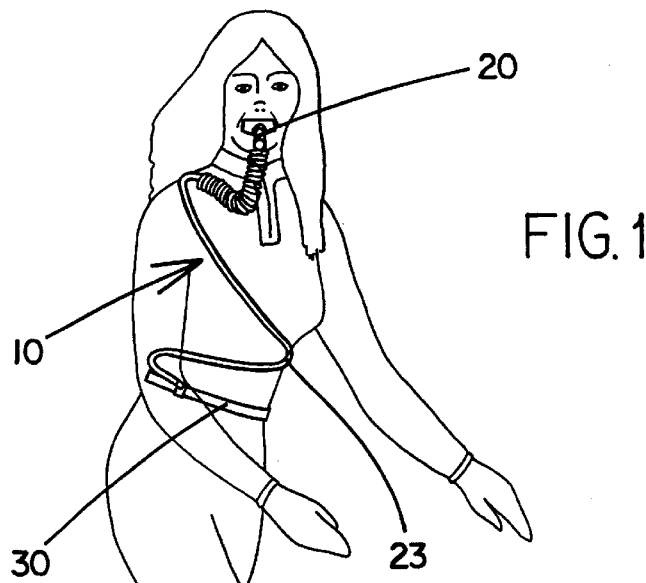
FIG. 1 is a schematic perspective view of a new cold weather air warming apparatus according to the present invention.

With reference now to the drawings, and in particular to FIGS. 1 through 4 thereof, a new cold weather air warming apparatus embodying the principles and concepts of the present invention and generally designated by the reference numeral 10 will be described.

As best illustrated in FIGS. 1 through 4, the cold weather air warming apparatus 10 generally comprises a mouthpiece 20 that has a mouth engaging portion 21, a coupling portion 22, and a lumen extending through opposite ends of the mouthpiece. A length of the body tubing 23 has opposite open first and second ends 24,25. The first end of the body tubing is coupled to the coupling portion of the mouthpiece. The length of body tubing is flexible and adapted for wrapping around a torso of a user, the open second end of the length of body tubing is in communication with the lumen of the mouthpiece.

Figure 2:
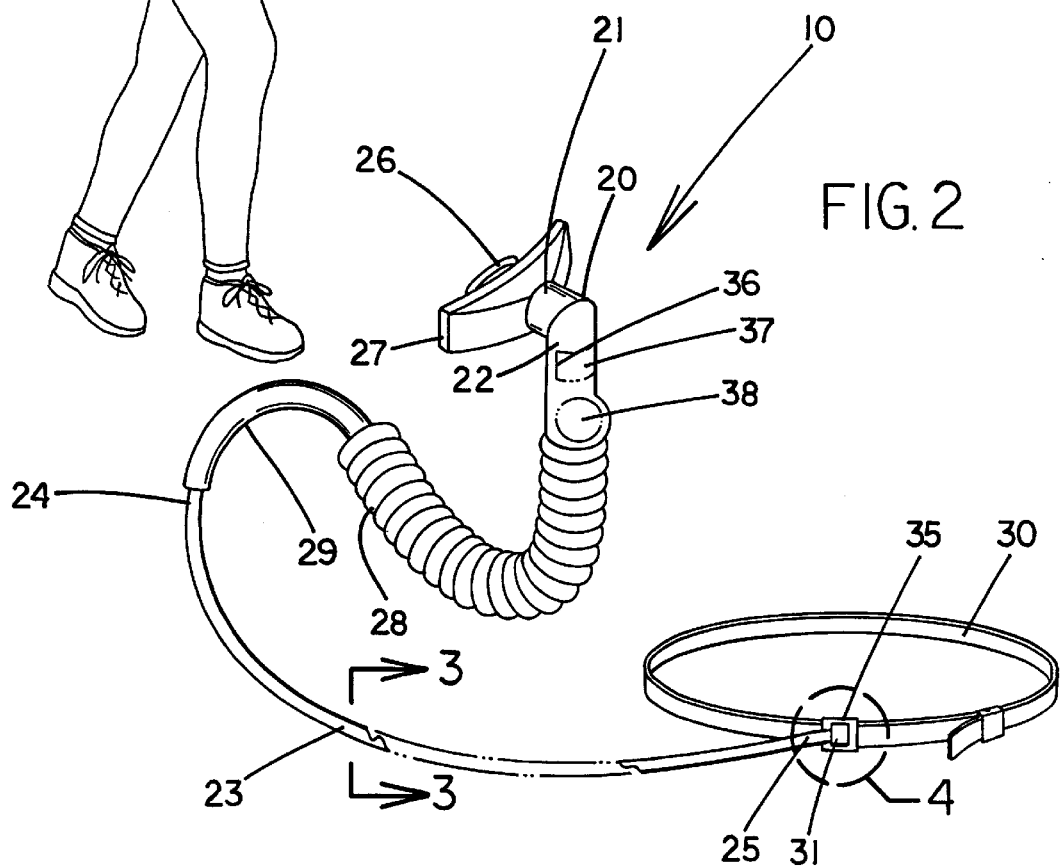
FIG. 2 is a schematic perspective view of the present invention.
Figure 3:
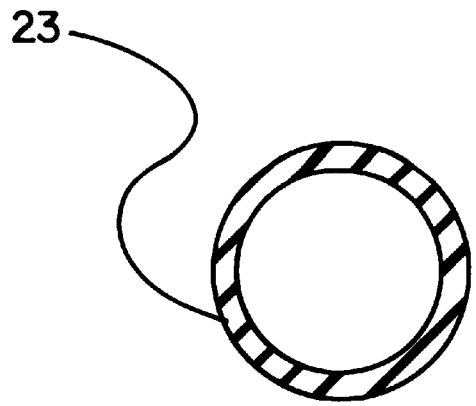
FIG. 3 is a schematic cross-sectional view of the present invention taken from line 3—3 of FIG. 2.

Preferably, as shown in FIG. 2, the mouth engaging portion of the mouthpiece has a bite tube 26 extending outwardly from it. The bit tube is adapted for insertion in the mouth of the user between teeth of the mouth. The teeth hold the bite tube in the mouth.

Ideally, the mouth engaging portion of the mouthpiece has a mouth engaging flange 27 laterally extending from it that is adapted for engaging an outer surface of a mouth of a user to form a seal with the mouth so that as little air as possible is permitted to enter the mouth other than from the air warming apparatus.

Preferably, the mouth engaging portion of the mouthpiece is oriented at about a 90 degree angle with respect to the coupling portion.

Also preferably, a length of resiliently deformable ribbed tubing 28 is coupled to the coupling portion of the mouthpiece. The pleats between the ribs of the ribbed tubing should permit the ribbed tubing to be more flexible than the body tubing so that it permits very little resistance to movement of the user's head, as well as so that it fits comfortably against the body and shoulder of the user.

Ideally, a length of hard tubing 29 is coupled to the ribbed tubing. The length of hard tubing is arcuate and adapted for hooking over a shoulder of a user to help keep the body tubing from pulling downwardly on the ribbed tubing. Most ideally, an outer diameter of the length of hard tubing is less than an outer diameter of the ribbed tubing. In such an embodiment, the first end of the body tubing is coupled to the hard tubing and the open second end of the length of body tubing is in communication with the lumen of the mouthpiece.

Figure 4:
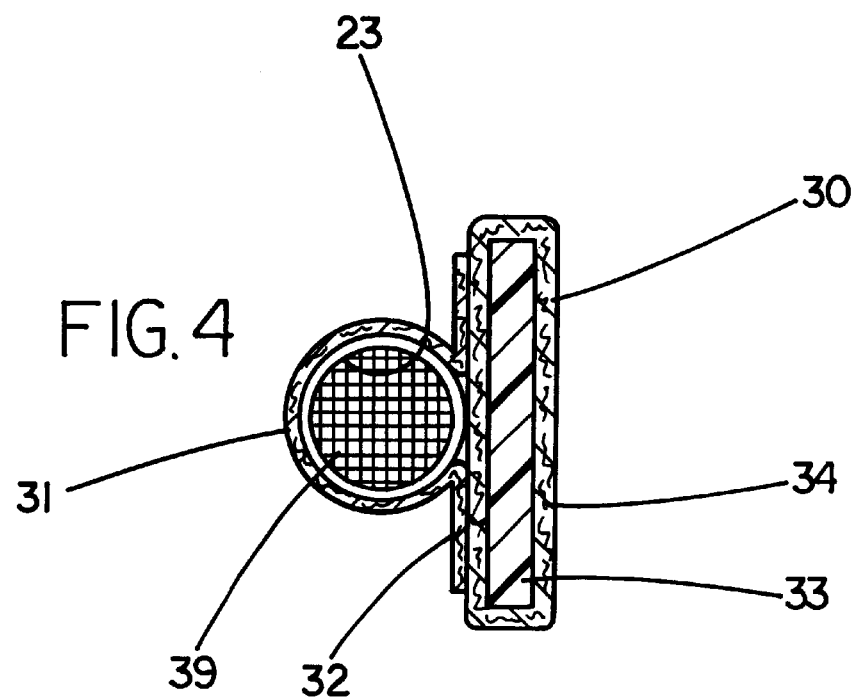
FIG. 4 is a schematic cross-sectional view of the present invention taken from circle 4 of FIG. 2.

Preferably, the second end of the length of body tubing is coupled to an elongate torso strap 30 that is adapted for wrapping around a torso of a user. More preferably, as shown in FIG. 4, the torso strap has a loop 31 formed on it that comprises a strap 32 of elastic material coupled to the torso strap. The second end of the length of body tubing is secured to the loop. The loop helps ensure that the open second end of the body tubing does not get blocked.

Also preferably, as illustrated in FIG. 4, the torso strap has a deformable inner portion 33 and an elastic outer covering 34. The torso strap is elastically extendable along its longitudinal axis.

Preferably, the torso strap has a buckle 35 coupled to one of its ends. Another end of the torso strap extends through the buckle. The buckle permits tightening and loosening of the torso strap around a torso of a user. A hooks and loops fastener (not shown) may be used instead of a buckle.

Instead of a torso strap, a string (not shown) may be coupled to the second end of the body tubing to hold the second end of the body tubing in place.

Preferably, the coupling portion of the mouthpiece has a ball valve 38. The ball valve permits air to flow through the coupling portion towards the mouth engaging portion but restricts air flow through the coupling portion away from the mouth engaging portion. The ball valve helps prevent air exhaled by a user from returning into the body tube, where the user would then reinhale it.

Ideally, the coupling portion of the mouthpiece has an aperture 36 extending through it and a door valve 37 for selectively closing the aperture. The door valve permits air to flow through the aperture of the coupling portion when air pressure in the mouthpiece exceeds a predetermined level. The door valve restricts air flowing through the aperture of the coupling portion when air pressure in the mouthpiece is below a predetermined level. Most ideally, the door valve is positioned between the ball valve and the mouth engaging portion of the mouthpiece. The door valve permits a user to exhale into the mouthpiece without forcing air into the body tubing.

Optionally, the second end of the body tube has a filter 39 detachably coupled to it that prevents dust, pollen, and other airborne debris from entering the body tube and being inhaled by a user. The filter may be a tightly woven screen, or may be of interwoven fibers. The filter may even include a charcoal portion that captures harmful fumes such as automobile exhaust, useful when jogging near a roadway.

An exemplary length of the length of body tubing between its ends is between about 2 and 10 feet, ideally about 6 feet. Longer and shorter lengths are used depending on the temperature of the ambient air. The colder the air, the longer the length the body tubing should be.

In use, the torso strap is wrapped around the torso of a user. The length of body tubing is also wrapped around the user's torso and the hard tubing is placed over a shoulder of the user, as shown in FIG. 1. The ribbed tubing may be placed between the user's neck and a shirt collar, or it may rest on the shoulder outside the shirt with the length of body tubing extending through the collar adjacent the neck. The bite tube is placed in the user's mouth. The user breathes through the air warming apparatus as normal.

The body's natural heat warms the air passing through the body tubing. Thus, a user would not continually inhale frosty air that can cause sharp pains in the lungs. Rather, warmed air is inhaled. The ball valve and door valve ensure that the user draws in fresh air each time he or she inhales, ensuring a fresh supply of oxygen.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An air warming apparatus, comprising:
   a mouthpiece having a mouth engaging portion, a coupling portion, and a lumen extending through opposite ends of said mouthpiece;
   a length of resiliently deformable ribbed tubing being coupled to said coupling portion of said mouthpiece;
   a length of hard tubing being coupled to said ribbed tubing, said length of hard tubing being arcuate and adapted for hooking over a shoulder of a user; and
   a length of body tubing having opposite open first and second ends, said first end of said body tubing being coupled to said hard tubing, said length of body tubing being flexible and adapted for wrapping around a torso of a user, said open second end of said length of body tubing being in communication with said lumen of said mouthpiece.

2. The air warming apparatus of claim 1, wherein said mouth engaging portion of said mouthpiece has a bite tube extending outwardly therefrom, said bite tube being adapted for insertion in a mouth of the user between teeth of the mouth such that said bite tube is adapted for being held in place by the teeth of the user.

3. The air warming apparatus of claim 2, wherein said mouth engaging portion of said mouthpiece has a mouth engaging flange laterally extending therefrom and adapted for engaging an outer surface of the mouth of the user.

4. The air warming apparatus of claim 1, wherein said torso strap has a loop formed thereon, said second end of said length of body tubing being secured to said loop.

5. The air warming apparatus of claim 1, wherein said coupling portion of said mouthpiece has a ball valve therein, said ball valve permitting air to flow through said coupling portion towards said mouth engaging portion when air pressure in said mouthpiece is below a predetermined level during inhalation by a user, said ball valve restricting air flowing through said coupling portion away from said mouth engaging portion when air pressure in said mouthpiece exceeds a predetermined level during exhalation of a user.

6. The air warming apparatus of claim 5, wherein said coupling portion of said mouthpiece has an aperture extending therethrough and a door valve for selectively closing said aperture, said door valve permitting air to flow through said aperture of said coupling portion when air pressure in said mouthpiece exceeds a predetermined level during exhalation by a user and said ball valve is restricting air flowing through said coupling portion, said door valve restricting air flowing through said aperture of said coupling portion when air pressure in said mouthpiece is below a predetermined level during inhalation by a user and said ball valve permits air to flow through said coupling portion, said door valve being positioned between said ball valve and said mouth engaging portion of said mouthpiece.

7. The air warming apparatus of claim 5, wherein said second end of said body tubing has a filter detachably coupled thereto and adapted for helping stop passage of airborne debris from entering said body tubing.

8. An air warming apparatus, comprising:
   a mouthpiece having a mouth engaging portion, a coupling portion, and a lumen extending through opposite ends of said mouthpiece;
   said mouth engaging portion of said mouthpiece having a bite tube extending outwardly therefrom, said bite tube being adapted for insertion in a mouth of a user between teeth of said mouth such that said bite tube is adapted for being held in place by the teeth of the user;
   said mouth engaging portion of said mouthpiece having a mouth engaging flange laterally extending therefrom and adapted for engaging an outer surface of the mouth of the user;
   said mouth engaging portion of said mouthpiece being oriented at about a 90 degree angle with respect to said coupling portion;
   a length of resiliently deformable ribbed tubing being coupled to said coupling portion of said mouthpiece;
   a length of hard tubing being coupled to said ribbed tubing, said length of hard tubing being arcuate and adapted for hooking over a shoulder of the user;
   an outer diameter of said length of hard tubing being less than an outer diameter of said ribbed tubing;
   a length of body tubing having opposite open first and second ends, said first end of said body tubing being coupled to said hard tubing, said length of body tubing being flexible and adapted for wrapping around a torso of the user, said open second end of said length of body tubing being in communication with said lumen of said mouthpiece;

an elongate torso strap adapted for wrapping around the torso of the user, said second end of said length of body tubing being coupled to said torso strap;

said torso strap having a loop formed thereon, said second end of said length of body tubing being secured to said loop;

said torso strap having an inner portion and an elastic outer covering, said torso strap being elastically extendable along a longitudinal axis thereof;

said torso strap having a buckle coupled to an end thereof, another end of said torso strap extending through said buckle, said buckle being for permitting tightening and loosening of said torso strap around the torso of the user;

said coupling portion of said mouthpiece having a ball valve therein, said ball valve permitting air to flow through said coupling portion towards said mouth engaging portion when air pressure in said mouthpiece is below a predetermined level during inhalation by a user, said ball valve restricting air flowing through said coupling portion away from said mouth engaging portion when air pressure in said mouthpiece exceeds a predetermined level during exhalation by a user;

said coupling portion of said mouthpiece having an aperture extending therethrough and a door valve for selectively closing said aperture, said door valve permitting air to flow through said aperture of said coupling portion when air pressure in said mouthpiece exceeds a predetermined level during exhalation by a user and said ball valve is restricting air flowing through said coupling portion, said door valve restricting air flowing through said aperture of said coupling portion when air pressure in said mouthpiece is below a predetermined level during inhalation by a user and said ball valve permitting air to flow through said coupling portion, said door valve being positioned between said ball valve and said mouth engaging portion of said mouthpiece; and said second of said body tubing having a filter detachably coupled thereto and adapted for helping stop passage of airborne debris from entering said body tubing.

9. An air warming apparatus, comprising:

a mouthpiece having a mouth engaging portion, a coupling portion, and a lumen extending through opposite ends of said mouthpiece;

a length of body tubing having opposite open first and second ends, said first end of said body tubing being coupled to said coupling portion of said mouthpiece, said length of body tubing being flexible and adapted for wrapping around a torso of a user, said open second end of said length of body tubing being in communication with said lumen of said mouthpiece; and an elongate torso strap adapted for wrapping around the torso of the user, said second end of said length of body tubing being coupled to said torso strap;

wherein said torso strap has a loop formed thereon, said second end of said length of body tubing being secured to said loop.

10. The air warming apparatus of claim 9, wherein said mouth engaging portion of said mouthpiece has a bite tube extending outwardly therefrom, said bite tube being adapted for insertion in a mouth of the user between teeth of the mouth such that said bite tube is adapted for being held in place by the teeth of the user.

11. The air warming apparatus of claim 10, wherein said mouth engaging portion of said mouthpiece has a mouth engaging flange laterally extending therefrom and adapted for engaging an outer surface of the mouth of the user.

12. The air warming apparatus of claim 9, wherein said coupling portion of said mouthpiece has a ball valve therein, said ball valve permitting air to flow through said coupling portion towards said mouth engaging portion when air pressure in said mouthpiece is below a predetermined level during inhalation by a user, said ball valve restricting air flowing through said coupling portion away from said mouth engaging portion when air pressure in said mouthpiece exceeds a predetermined level during exhalation by a user.

13. The air warming apparatus of claim 12, wherein said coupling portion of said mouthpiece has an aperture extending therethrough and a door valve for selectively closing said aperture, said door valve permitting air to flow through said aperture of said coupling portion when air pressure in said mouthpiece exceeds a predetermined level during exhalation by a user and said ball valve is restricting air flowing through said coupling portion, said door valve restricting air flowing through said aperture of said coupling portion when air pressure in said mouthpiece is below a predetermined level during inhalation by a user and said ball valve permits air to flow through said coupling portion, said door valve being positioned between said ball valve and said mouth engaging portion of said mouthpiece.

14. The air warming apparatus of claim 12, wherein said second end of said body tubing has a filter detachably coupled thereto and adapted for helping stop passage of airborne debris from entering said body tubing.

* * * * *